(12) United States Patent
Pina et al.

(10) Patent No.: US 10,172,570 B2
(45) Date of Patent: Jan. 8, 2019

(54) METHODS AND APPARATUS FOR DYNAMIC DISPLAYS

(71) Applicant: Under Armour, Inc., Baltimore, MD (US)

(72) Inventors: Marcus Pina, Austin, TX (US); Gloria Wu, Austin, TX (US); Andrew Moore, Austin, TX (US); Scott Laing, Austin, TX (US)

(73) Assignee: Under Armour, Inc., Baltimore, MD (US)

( * ) Notice: Subject to any disclaimer, the term of this patent is extended or adjusted under 35 U.S.C. 154(b) by 90 days.

(21) Appl. No.: 15/211,523

(22) Filed: Jul. 15, 2016

(65) Prior Publication Data

US 2018/0014794 A1 Jan. 18, 2018

(51) Int. Cl.
*A61B 5/02* (2006.01)
*A61B 5/11* (2006.01)
*G06T 11/00* (2006.01)
*G06T 13/80* (2011.01)
*A61B 5/00* (2006.01)
*A61B 5/024* (2006.01)

(52) U.S. Cl.
CPC ............ *A61B 5/7425* (2013.01); *A61B 5/024* (2013.01); *A61B 5/1118* (2013.01); *A61B 5/4806* (2013.01); *A61B 5/486* (2013.01); *A61B 5/4866* (2013.01); *A61B 5/744* (2013.01); *G06T 11/001* (2013.01); *G06T 13/80* (2013.01); *G06T 2210/41* (2013.01)

(58) Field of Classification Search
CPC combination set(s) only.
See application file for complete search history.

(56) References Cited

U.S. PATENT DOCUMENTS

| | | | |
|---|---|---|---|
| 2009/0054751 A1* | 2/2009 | Babashan | A61B 5/0002 600/324 |
| 2013/0106684 A1* | 5/2013 | Weast | G06F 19/3481 345/156 |
| 2013/0122476 A1* | 5/2013 | Guillama | A63B 24/00 434/247 |
| 2014/0083779 A1* | 3/2014 | Sharma | G01G 19/44 177/1 |
| 2017/0259116 A1* | 9/2017 | Mestas | A63B 24/0062 |
| 2017/0303846 A1* | 10/2017 | O'Brien | A61B 5/0075 |
| 2017/0351295 A1* | 12/2017 | Malhotra | G06F 1/163 |

* cited by examiner

*Primary Examiner* — Wesner Sajous
(74) *Attorney, Agent, or Firm* — Maginot, Moore & Beck LLP

(57) ABSTRACT

Apparatus and methods for providing dynamic displays. In one embodiment, a method is provided wherein health parameters having goals associated therewith are displayed; data relating to the health parameters is received and the display is incremented according to a progress of the user toward the goal. When collection of the data is completed, it is determined whether a current value of a first one of the heath parameters within a predetermined range of the goal associated therewith. When the current value of the first one of the health parameters is within the range, a portion of the display relating thereto is upgraded. When the current value of all of the health parameters is within the range, upgrading the entire display. The display upgrades may comprise display of an animation and/or using color, light, and/or flashing to simulate a shining or shimmering of the display.

17 Claims, 7 Drawing Sheets

METHODS AND APPARATUS FOR DYNAMIC DISPLAYS

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

TECHNICAL FIELD

The present disclosure relates to the field of display generation and delivery. More particularly, the present disclosure relates to methods, devices, systems, and computer programs for the management of a plurality of user goals via a unified, dynamically adjusting display.

BACKGROUND

The background description provided herein is for the purpose of generally presenting the context of the disclosure. Unless otherwise indicated herein, the materials described in this or any section of the disclosure are not prior art to the claims in this application and are not admitted to be prior art by inclusion herein.

Recent advancements in electronics technology has led to the widespread use of portable devices. In particular, a large variety of biometric monitoring devices that users may wear on their bodies to measure activity (e.g., a number of steps taken, flights of stairs, hours of sleep, etc.), biometric parameters (e.g., hear rate, blood pressure, etc.), and other environmental parameters (e.g., temperature, altitude, etc.) have become widely available for general use. Users are able to utilize the foregoing devices to improve overall health.

Generally speaking, having a multitude of devices to monitor and track health parameters would appear to provide users with advanced health tracking abilities. However, managing the amount of data provided from the plurality of user devices and ensuring that specific health goals are met across the plurality of devices creates a significant problem to the user. Moreover, it is noted that users generally react positively to visual rewards as a reinforcement of good habits. Hence, what are needed are methods, devices, systems, and computer programs for the management of a plurality of user devices and the establishment of healthy and helpful patterns of use for each via a unified user interface which is configured to provide a dynamically adjusting display as the user reaches his/her goals.

SUMMARY OF THE DISCLOSURE

The present disclosure addresses the foregoing needs by disclosing, inter alia, methods, devices, systems, and computer programs for the management of a plurality of user goals via a unified, dynamically adjusting display.

Specifically, methods, apparatus, computer applications, and systems are provided to enable a user to manage a plurality of health devices and monitor his/her progress via: enabling the user to set one or more goals relating to measured health parameters; displaying the set goals; collecting health parameter measurement data; determining whether a goal for the measured health parameter is met; if not, incrementing the display and continuing to collect data; if so, determining whether any additional unmet goals exist; if so, upgrading the individual goal display and continuing to collect data; if not, upgrading the entire display.

In another embodiment, a method is provided wherein health parameters having goals associated therewith are displayed; data relating to the health parameters is received and the display is incremented according to a progress of the user toward the goal. When collection of the data is completed, it is determined whether a current value of a first one of the heath parameters within a predetermined range of the goal associated therewith. When the current value of the first one of the health parameters is within the range, a portion of the display relating thereto is upgraded. When the current value of all of the health parameters is within the range, upgrading the entire display. The display upgrades may comprise display of an animation and/or using color, light, and/or flashing to simulate a shining or shimmering of the display.

These and other aspects of the disclosure shall become apparent when considered in light of the disclosure provided herein.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example, and not by way of limitation, in the figures of the accompanying drawings.

All Figures © Under Armour, Inc. 2016. All rights reserved.

DETAILED DESCRIPTION

Exemplary Embodiments

Disclosed embodiments include systems, apparatus, method and storage medium associated with goal management across a plurality of devices in general, and unified, dynamically adjusting display in particular.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

Figure 1:
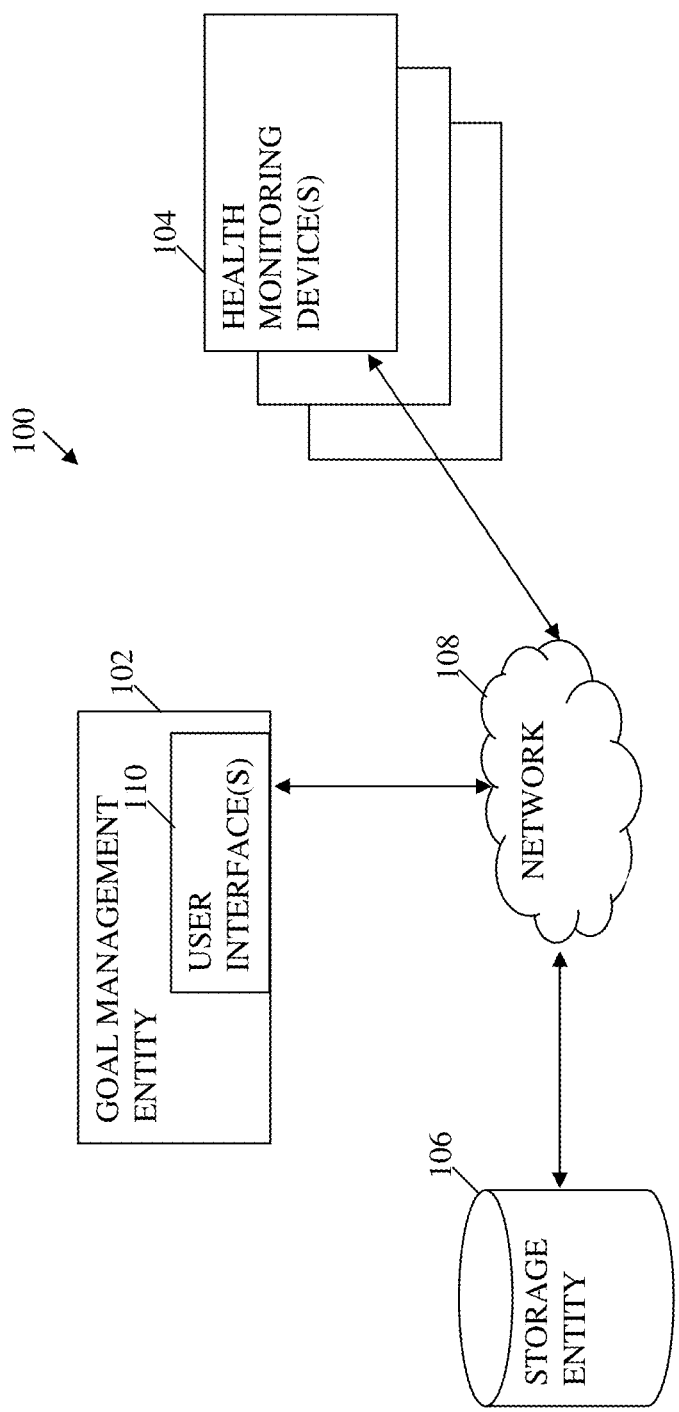
FIG. 1 is a block diagram illustrating an exemplary system for providing a dynamically adjusting display to manage a plurality of goals in accordance with one embodiment of the present disclosure.

Referring now to FIG. 1, an exemplary dynamic display system 100 in accordance with one embodiment of the present disclosure is illustrated. As shown, the system 100 generally comprises a goal management entity 102 in communication with a plurality of health monitoring devices 104 and a storage entity 106 via a network 108.

The goal management entity 102 may comprise a software application or suite of applications configured to run on a client device whether stationary or portable. For example, the management entity 102 may run on desktop computers (such as those available from Dell Computing of Austin, Tex.), or smartphones, computing tablets, laptop computers, electronic readers, personal digital assistants, and so forth, such as Galaxy S4® from Samsung Electronics of Seoul, Korea, or iPad® from Apple Computer of Cupertino, Calif.

The plurality of monitoring devices 104 may comprise one or more portable computing devices designed to measure, sense, monitor, or otherwise obtain biometric, environmental, and/or activity parameters. In one variant, certain ones of the health monitoring devices 104 comprise wearable health-related parameter measurement and computing devices, such as e.g., a smart watch, an activity tracker, a heart rate monitor, a sleep tracking device, a nutrition tracking device, a smart scale, and/or smart eyeglasses. In addition, an exemplary monitoring device 104 may comprise a smart phone having one or more of the foregoing monitoring capabilities. In a further embodiment, the goal management entity 102 may be configured as an application suite configured to run on an individual one of the plurality of monitoring devices 104 (such as e.g., a smartphone).

The monitoring devices 104 provide sensed data to the management entity 102 and/or to the storage entity 106 (for storage thereat) via the network 108. The sensed data comprises data which the particular device 104 is configured to collect or obtain (such as activity, biometric, and environmental data). For example, an activity tracking device is configured to collect activity data such as steps taken, distance travelled, rate or pace of a run, and/or flights of stairs climbed, etc.; a heart rate monitor is configured to collect heartbeat data; a sleep tracking device collects data relating to how much time a user/wearer spends sleeping; a nutrition tracking device collects data relating to food and drinks consumed by a user; a smart scale collects data relating to a body weight, body fat percentage, and/or body mass index (BMI), etc. In addition, certain ones of the devices 104 may collect more than one type of sensed data. For example, a smart watch and/or smart phone, may be utilized as an activity tracking device, a heart rate monitor, a sleep tracking device, and/or a nutrition tracking device.

It is noted that the data may be requested by the management entity 102 or provided thereto without an affirmative request. For example, the sensed data may be provided to the management entity 102 as it is collected, i.e., in real time. Alternatively, sensed data may be provided as a single so-called "data dump" at a predetermined time for each monitoring device 104. In another example, the management entity 102 may periodically request data from the monitoring devices 104 at different periods or intervals based on the type of device. Alternatively, or in addition, the data may be provided first or simultaneously to the storage entity 106.

In another embodiment, the monitoring devices 104 may provide to the management entity 102 information relating to the status of the devices 104 themselves. For example, the information may relate to a battery level, memory level, connection strength, and/or a date/time of last use of the device 104.

The network 108 which enables communication between the goal management entity 102 and the monitoring devices 104 may comprise a wired and/or wireless, private and/or public network, including e.g., the Internet. Accordingly, each of the monitoring devices 104 and the goal management entity 102 may be configured with an appropriate networking communication interface (not shown). An example of wired communication interface may include, but is not limited to, Ethernet; while examples of wireless communication interfaces may include, but are not limited to, near field communication (NFC), Bluetooth, WiFi, 4G or 5G LTE. It is further appreciated that various gateways, routers, switches, based stations, and so forth may be placed between the communication interfaces of foregoing devices.

Communication between the health monitoring devices 104 and the goal management entity 102 may be facilitated via the establishment of a unique identifier for each of the monitoring devices 104. In one embodiment, the unique identifier corresponds to a vendor/Ethernet/Bluetooth/Mac address, serial number, and/or other identifier of the device 104. Alternatively, the user may (via a user interface) enter a unique identifier to each monitoring device 104, e.g., "ACTIVITY TRACKER", "BODY ANALYZER", etc. In a further example, the management entity 102 may assign the unique identifier without additional input or information. The utilization of a unique identifier enables data received therefrom to be properly associated to the correct device, and enables routing of messages to individual ones of the devices 104.

As noted above, a primary feature of the present invention is to provide a dynamic display for goal management across a plurality of health-related goals and/or health monitoring devices 104. Hence, in one exemplary embodiment, for each monitoring device 104 and/or for each data type (e.g., heart rate data, sleep data, step data, weight data, nutrition data, etc.), a user enters a goal via a user interface 110 (exemplary GUI are discussed in further detail below). In addition, or as an alternative, the goals may be recommended. For example, default goals may be pre-loaded or pushed/pulled from an Internet database (not shown) to the monitoring devices 104 and/or the management entity 102. In another embodiment, one or more goals are derived by the management entity 102 and/or the monitoring devices 104 such as based on e.g., the type of health monitoring device 104, features of the user (age, height, weight, normal activity level, etc.), etc. These defaults goals may be adjusted by a user in one variant. In a further variant, the goals are entered at individual ones of the monitoring devices 104 (via an interface thereof; not shown), and subsequently provided to the goal management entity 102.

In yet another variant, one or more of the entered goals may be associated with an acceptable range. According to this variant, sensed data within the acceptable range may be said to meet the stated goal. In a manner similar to that discussed above, the acceptable range for each goal may be entered by a user, preloaded, recommended, derived, and/or pulled from a database (not shown) via the network 108.

For the purposes of simplicity of the present discussion, several types of goals are discussed; however, it is appreciated that various other types of goals (not discussed herein) may be utilized in accordance with the present invention, those discussed herein are merely exemplary of the general principles of the disclosure. Moreover, as noted above, the specific goals and/or ranges discussed herein may be entered by a user, pulled/pushed to the goal management entity 102 from the Internet, preloaded to the goal management entity 102, provided from the monitoring devices 104 (e.g., pre-stored thereon), and/or determined or derived by the management entity 102 and/or monitoring devices 104.

Information relating each device 104 (including e.g., its unique identifier) is stored at a local storage entity 106. Additionally, storage entity 106 is further configured to store the aforementioned goals and goal ranges. In one embodiment, the local storage entity 106 comprises a separate device from the management entity 102. Alternatively, the storage entity 106 may be integrated within the management entity 102 and/or the health monitoring device(s) 104.

In a further embodiment, so-called "maximum compliance" and "minimum compliance" goals are utilized. Maximum compliance goals comprise goals which the user is to adhere to without exceeding; also referred to herein as "strict compliance" goals. Variation by going over a minimum compliance goal is discouraged; however, variation by remaining below the goal is encouraged (in some cases). Examples of maximum compliance goals which are not to be exceeded include weight goals, calorie intake goals, resting heart rate goals, etc. Minimum compliance goals comprise goals which serve as a minimum value to meet; also referred to herein as "mere compliance" goals. Variation by going over a minimum compliance goal is encouraged (in some cases); however, variation by not meeting the goal is discouraged. Examples of minimum compliance goals which are at least to be met include activity goals (such as stairs, steps, and workouts), pace goals, sleep goals, etc.

In addition, compliance range goals may be utilized. Compliance range goals comprise goals for which one or more compliance ranges which define healthy habits are given. Variation by going outside (i.e., either over or under) a compliance range goal is discouraged. Examples of compliance range goals may include any of the herein described goals, such as, weight goals, calorie intake goals, resting heart rate goals, activity goals (such as stairs, steps, workouts), pace goals, sleep goals, etc.

As discussed in further detail below, the herein provided system 100 generates a unified display for each of the plurality of measured parameters (such as e.g., activity, sleep, weight, steps, workouts, heart rate, mood, etc.). The display dynamically updates according to sensed data such that one or more of the displayed health-related parameters is incremented toward a goal. In one specific example, individual ones of the health-related parameters are displayed together to form a shape (such as a square, a diamond, a circle, concentric shapes, etc.). For example, in the instance the overall shape comprises a circle, four health-related parameters may comprise sectors (or pie slices) which fit together to form the circle. In another embodiment, an additional small shape may be placed in the center of the overall shape in order to add another health-related parameter to the display, such as a concentric center circle, thereby creating four segments of an annulus (instead of the previously discussed four sectors).

The portions of the shape which are dedicated to the individual parameters are incremented, e.g., filled-in, such as with color or shading, as the user moves toward accomplishing a goal. Continuing the simple example from above, assuming the health-related parameters comprise individual segments of an annulus and a concentric circle which combine a form a larger circle; a portion of the annulus relating to e.g., steps may slowly be filled-in as the day continues. That is to say, when the user has completed 500 steps and has a 5,000 step goal for the day, the portion of the annulus representative of the user's step goal is filled-in by 10%. Later, when the user has taken 2,500 steps, the annulus is filled-in by 50%, and so forth. Similarly, each of the other displayed health-related parameters are incremented as the user moves toward accomplishing his/her goal.

When the user reaches his/her goal for a given measured parameter (e.g., by staying within a compliance range, meeting or exceeding a minimum compliance goal and/or meeting or staying below a maximum compliance goal) the display is upgraded in order to document or celebrate the accomplishment. The display upgrade for an individual parameter may include e.g., causing its portion of the shape, such as the portion of the annulus, to blink or flash, to change colors, to be highlighted or illuminated, change size or shape, etc. Additionally, when all of the displayed parameter goals are met, a priority upgrade may be displayed such as those listed above, and/or animation of the entire shape, enlarging the entire shape, banners, notifications/messages, etc. Still further, when a user exceeds a minimum compliance goal and/or remains below a maximum compliance goal an additional or different priority upgrade may be displayed (such as those discussed above and/or others).

Methods by which the management entity 102 and health monitoring devices 104 cooperate to accomplish the foregoing dynamic display features are discussed in detail with respect to FIGS. 2, 3A, and 3B below.

Figure 2:
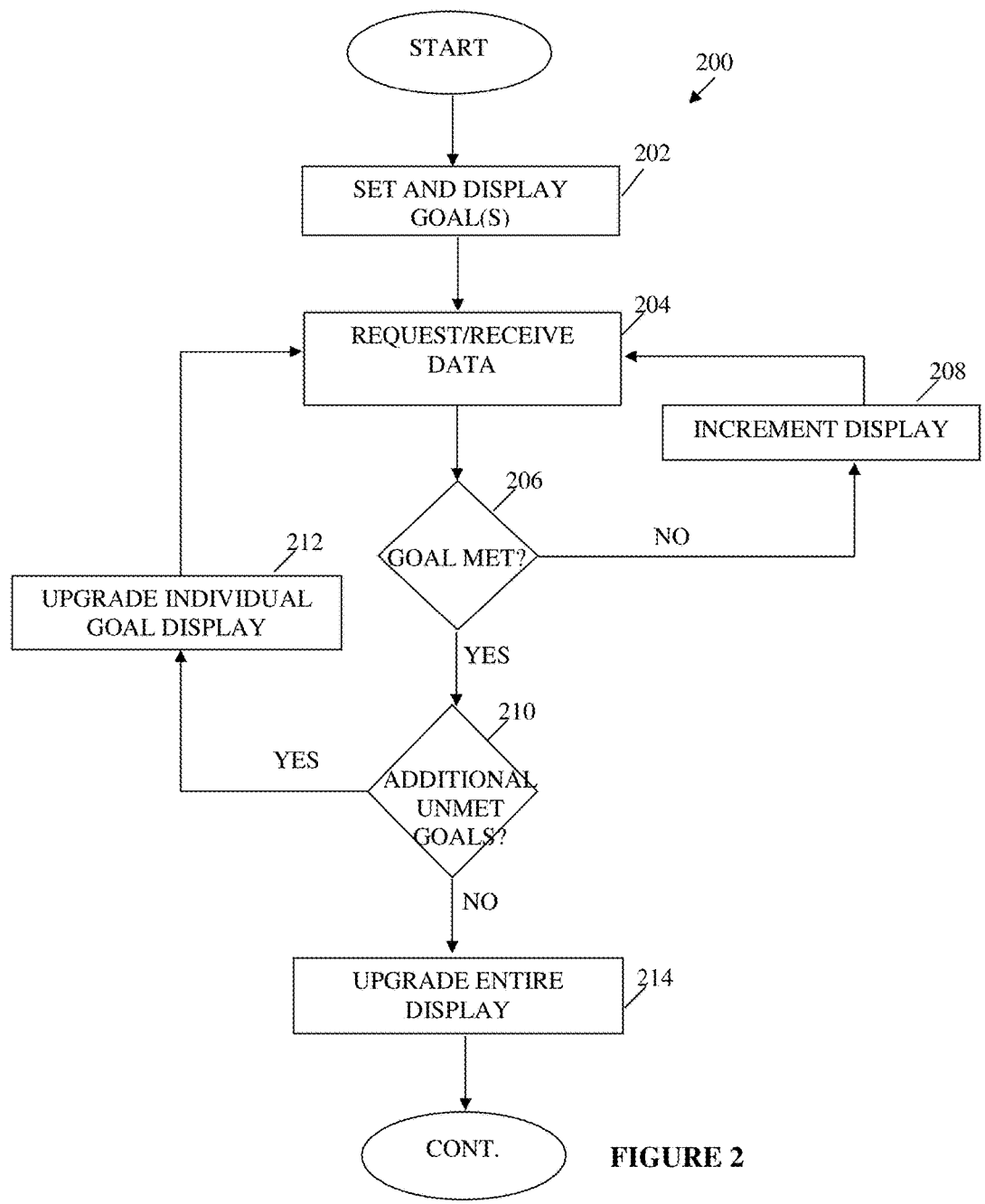
FIG. 2 is a logical flow diagram illustrating a generalized method for dynamically adjusting a display to manage a plurality of goals in accordance with one embodiment of the present disclosure.

Referring now to FIG. 2, a generalized method 200 for dynamically adjusting a display to manage a plurality of goals is provided.

As noted previously, in one embodiment the plurality of monitoring devices 104 are first registered to the management entity 102 (this step is not illustrated for the sake of simplicity). This registration may occur at start-up of a new monitoring device 104 or the management entity 102, and/or may be due to a periodic request from the management entity 102. In one exemplary embodiment, the device registration further includes assignment of a unique identifier to each of the monitoring devices 104 which are to be managed in order to facilitate communication therewith.

At step 202 of the method 200, goals are set for each of the health-related parameters to be measured. As noted above, the goals may be entered by the user, recommended by the management device 102 and/or the health-parameter monitoring device 104, provided from a device manufacturer database (not shown), and/or derived (by the management device 102 and/or monitoring devices 104) based on information known about the user, the device type, etc. In addition, an appropriate range for one or more of the entered goals may also be set at step 202. The goals (and associated ranges) are stored at the local storage entity 106 in one embodiment.

The set goals may then be displayed (optional). Hence, at a start or home screen prior to the user beginning his/her day, each portion of the display will show the goal with no shading or coloring to indicate progress. In another alternative, the display may be greyed-out or otherwise colored to indicate that the displayed number represents a goal (and not the user's progress). Still further, the display may indicate that the displayed number is a goal. For example, text may be displayed which states that the amount is a goal.

Next, at step 204, data is requested and/or received from the plurality of health monitoring devices 104. In one embodiment, the data received from a monitoring device 104 comprises health parameter information which is sensed, monitored, or otherwise obtained relating to a wearer or user of the device 104. For example, the device may provide information relating to a number of steps taken, a heart rate, an amount of sleep, a number of calories ingested, a weight of the user, an energy output score, etc.

The goal management entity 102 processes the data at step 206 to determine whether a goal associated to the collected data is met. In one embodiment, this occurs via (i) an addition of the newly collected data (collected at step 204) to previously stored health parameter data (i.e., data compiled from previous data collection instances) to arrive at a new running/current total for the given health parameter; and (ii) a comparison of the current total to a stored goal for that particular health parameter. The current total and/or running totals are stored at e.g., the storage entity 106 in one embodiment. In a further variant, the goal to which the summed data is stored has added thereto any applicable stored ranges. Alternatively, the current total is derived or calculated anew at each data collection instance (step 204); i.e., a running total is not stored.

When it is determined that the goal is not met (at step 206), per step 208 the display for the particular health parameter is incremented. Incrementing the display may include calculating a percentage representative of the current total to the goal amount, and then using shading, coloring, and/or other means to display the percentage of the goal currently accomplished. Thereafter, the method 200 repeats at step 204 and additional sensed/measured health parameter data is collected.

When it is determined that the goal is met (at step 206), it is next determined whether there remain any additional unmet goals (step 210). As noted above, a single display is intended to indicate goal status regarding multiple ones of measured health-parameters. Thus, although a goal for one health-parameter may be met, the other goals on the display may not yet be made. Where this is the case, per step 212, only the display for the individual goal which has been met is upgraded. In one embodiment, the upgrade may comprise a change in color, blinking, flashing, highlighting, or otherwise signifying the accomplishment. The method 200 continues at step 204, where additional data is collected.

When it is determined that no goals remain unmet (i.e., all of the displayed goals have been met) at step 210, then, per step 214 then the entire display is upgraded. In this embodiment, the entire display may be altered to provide a prioritized notification to the user that all goals have been met. For example, the upgrade may include a background change, a cyclical color change/flash, enlarging, animation, etc.

Figure 3A:
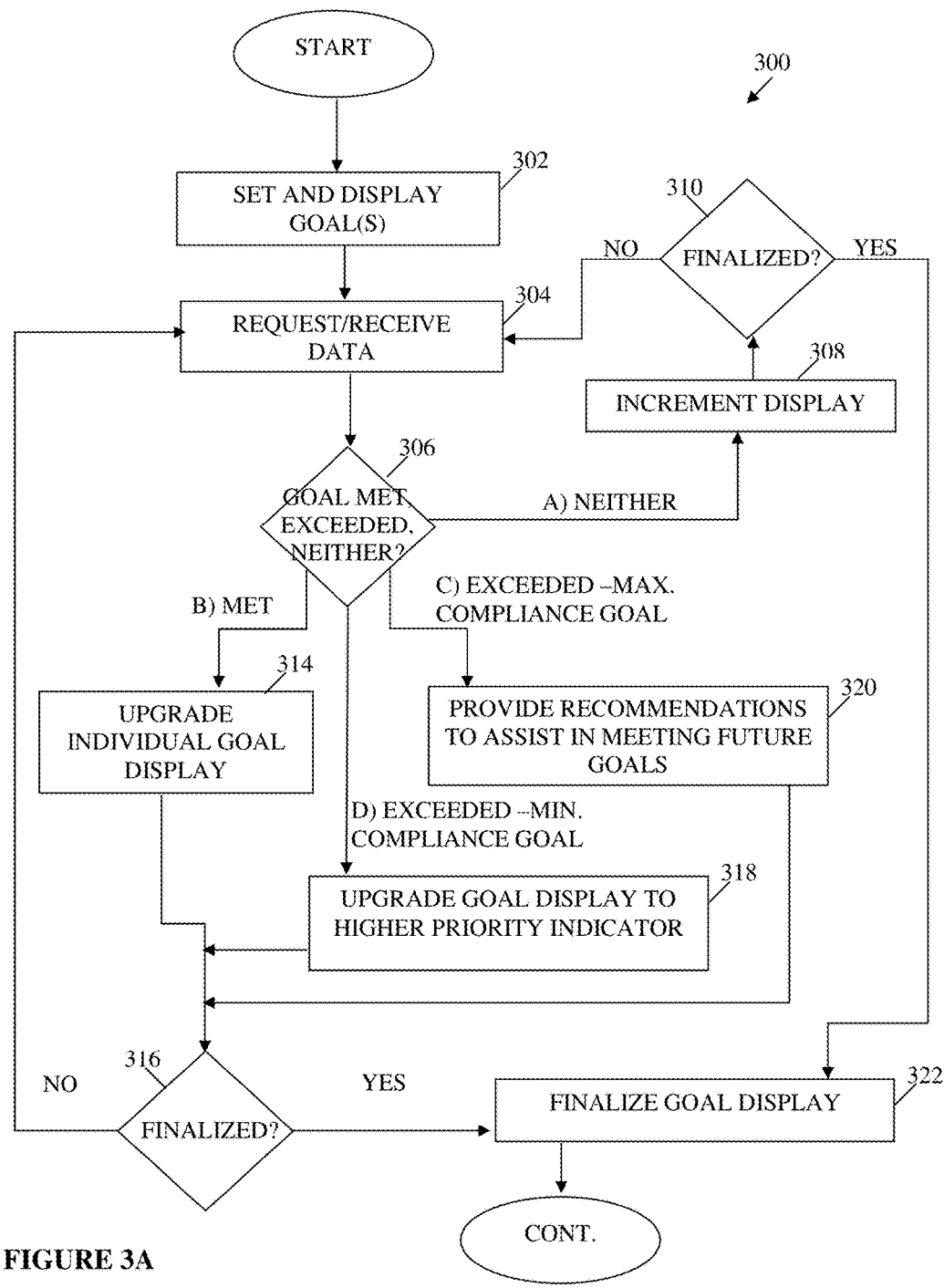
FIG. 3A is a logical flow diagram illustrating one exemplary method for managing one or more strict compliance goals and one or more mere compliance goals in accordance with the present disclosure.

Referring now to FIG. 3A, an exemplary method 300 for managing one or more strict compliance goals and one or more mere compliance goals is shown. As discussed above, each of the health monitoring devices 104 may be registered to the management entity 102 and assigned a unique identifier which is used in subsequent communication therebetween in advance (not shown).

As illustrated, per step 302, one or more goals are set and displayed. As discussed above, goals are entered in one embodiment by a user. Alternatively, or in addition, goals may be recommended (such as by pulling data from e.g., an Internet database) by the management device 102 and/or the health-parameter monitoring device 104. Data relating to the recommended goals may be provided in one embodiment from a device manufacturer. Additionally or in the alternative, the management device 102 and/or the monitoring devices 104 may derive goals based on characteristics of the user (such as age, height, weight, activity level, etc.) and the type of device. The set goals are stored at the storage entity 106. The set goals are displayed (step 302) at a home or start screen, i.e., prior to the user beginning progress toward meeting the goal.

Next, per step 304, data is requested by and/or received at the goal monitoring entity 102 from the health monitoring devices 104. The data comprises health parameter data which is sensed, monitored, or otherwise obtained by the device 104 and which relates to a wearer or user of the device 104. Specifically, the device may provide data relating to a number of steps taken, a heart rate, an amount of sleep, a number of calories ingested, a weight of the user, an energy output score, etc.

The requested/received data is processed at step 306 to determine whether a goal associated with the requested/received data is met, exceeded, or neither. In one exemplary embodiment, newly collected data (such as that requested/received at step 304) is added to a saved or stored running total for that data type to arrive at a new current/running total, which is subsequently saved. In one variant, the running total and current totals are saved at the storage entity 106. The new current/running total is then compared to a stored goal for that particular health parameter.

When the goal for the particular one of the health parameters to which the requested/received data correlates is neither met nor exceeded (pathway A), then per step 308, the display is incremented. As discussed elsewhere herein, incrementing the display may include e.g., calculating a percent of the goal which has been met, then illustrating the percent graphically on the display such as by shading or coloring in that amount of the displayed shape for the given health parameter. Take, for example, an instance where it is determined that 50% of a goal for steps for the day has been met. In this example, the portion of the annulus (or other shape) representative of the step goal is therefore shaded or colored in 50%.

Next it is determined at step 310 whether the data collection on that particular health parameter is finalized. In one embodiment, finalization may be dependent on e.g., time of day, a period over which the data was collected, or other trigger. For example, all data collection may be finalized at midnight. In another embodiment, a user may be asked to select whether the data collection for the day is completed.

In one optional embodiment, if the goal is not met or exceeded and the data collection is determined to be finalized, additional notifications may be provided to the user. For example, in the instance the goal was a maximum compliance goal, failure to meet or exceed the goal may be a positive use of the system. Specifically, in the instance the goal comprises a calorie intake goal, a finalized collection which is below the goal may be encouraged. Accordingly, the user may be congratulated for saying below the threshold limit. Similar to the methods and apparatus discussed herein, the display may be upgraded in this instance. In another example, in the instance the goal was a minimum compliance goal, failure to meet or exceed the goal may be a negative use of the system. Specifically, in the instance the goal comprises a step or activity counter, a finalized collection which is below the goal may be discouraged. Accordingly, the user may be provided with a recommendation to increase his/her activity or steps; the user may be recommended to decrease the goal or be provided with other helpful recommendations.

When the goal for a particular one of the health parameters is finalized, the method 300 continues to step 322 wherein the display for that goal is finalized. Once the display is finalized, it cannot be modified or changed. Moreover, data is no longer collected regarding the subject health-parameter, and/or if the data is collected it is not reflected toward on the display screen. When the goal for the particular one of the health parameters is not yet finalized, the method 300 returns to step 304 where additional measured health parameter data is requested and/or received.

When the goal for the particular one of the health parameters to which the requested/received data (step 304) is met (pathway B), per step 314 the individual goal display is upgraded. As noted previously, the individual goal display upgrades may include e.g., animation, enlarging, coloring, shading, highlighting, text/banner, or other indicator. In another embodiment, when no further goals remain unmet the entire display is upgraded as noted elsewhere herein.

Once the individual goal display is upgraded, it is determined whether the data collection on that particular health parameter is finalized at step 316. In one embodiment, the finalization may be based on e.g., a time of day, a period over which the data was collected, or other trigger. In another variant, the user may be asked whether he/she would like to finalize the goal and stop collecting data toward that parameter, or continue to collect data even though the goal has been met. If it is indicated that the goal is finalized, then per step 322, the goal display is finalized and no further alterations or changes may be made to it. If it is indicated that the goal is not finalized, then the method 300 returns to step 304 and additional measured health parameter data regarding the particular health parameter is requested and/or received.

When the goal for the particular one of the health parameters to which the requested/received data (step 304) is exceeded and the goal comprises a maximum compliance goal, pathway C is followed. As noted above, the user is to adhere to a maximum compliance goal without exceeding. Hence, in the event the maximum compliance goal is exceeded, per step 320, recommendations are provided to assist the user in meeting the goal in the future.

Next, per step 316, it is determined whether the data collection is finalized and if so, the goal display is finalized (step 322). Alternatively, when the data collection for that particular health parameter is not finalized, the method 300 continues at step 304 and additional measured health parameter data regarding the particular health parameter is requested and/or received.

When the goal for the particular one of the health parameters to which the requested/received data (step 304) is exceeded and the goal comprises a minimum compliance goal, pathway D is followed. As noted above, the user is encouraged to exceed a minimum compliance goal. Hence, in the event the minimum compliance goal is exceeded, per step 318, the goal display is upgraded to a higher priority indicator. According to this embodiment, the goal display upgrade comprises a different and more desirable upgrade than that which is used when the goal is merely met. For example, if the first tier upgrade comprises a color change to e.g., blue, then the higher tier upgrade may comprise changing the blue to a metallic or shiny blue (such as one which utilizes an animation to indicate its shimmer/shine).

Next, per step 316, it is determined whether the data collection is finalized and if so, the goal display is finalized (step 322). Alternatively, when the data collection for that particular health parameter is not finalized, the method 300 continues at step 304 and additional measured health parameter data regarding the particular health parameter is requested and/or received.

It is noted that although the above-disclosed method 300 includes instances where exceeding or falling below a set goal may be considered a positive interaction with the system, it is appreciated that a range may be given within which the divergence is acceptable. For example, although a lower than set goal calorie intake may be considered positive, very low calorie intake may be dangerous and/or may be indicative that the user is not entering his/her activity with consistency. It is further noted that, the herein disclosed method may be applied to each of a plurality of health parameter goals on a single display; when the goals of each are met, exceeded, and/or not exceeded (as appropriate to the goal type), the entire display may be upgraded (as discussed elsewhere herein).

Figure 3B:
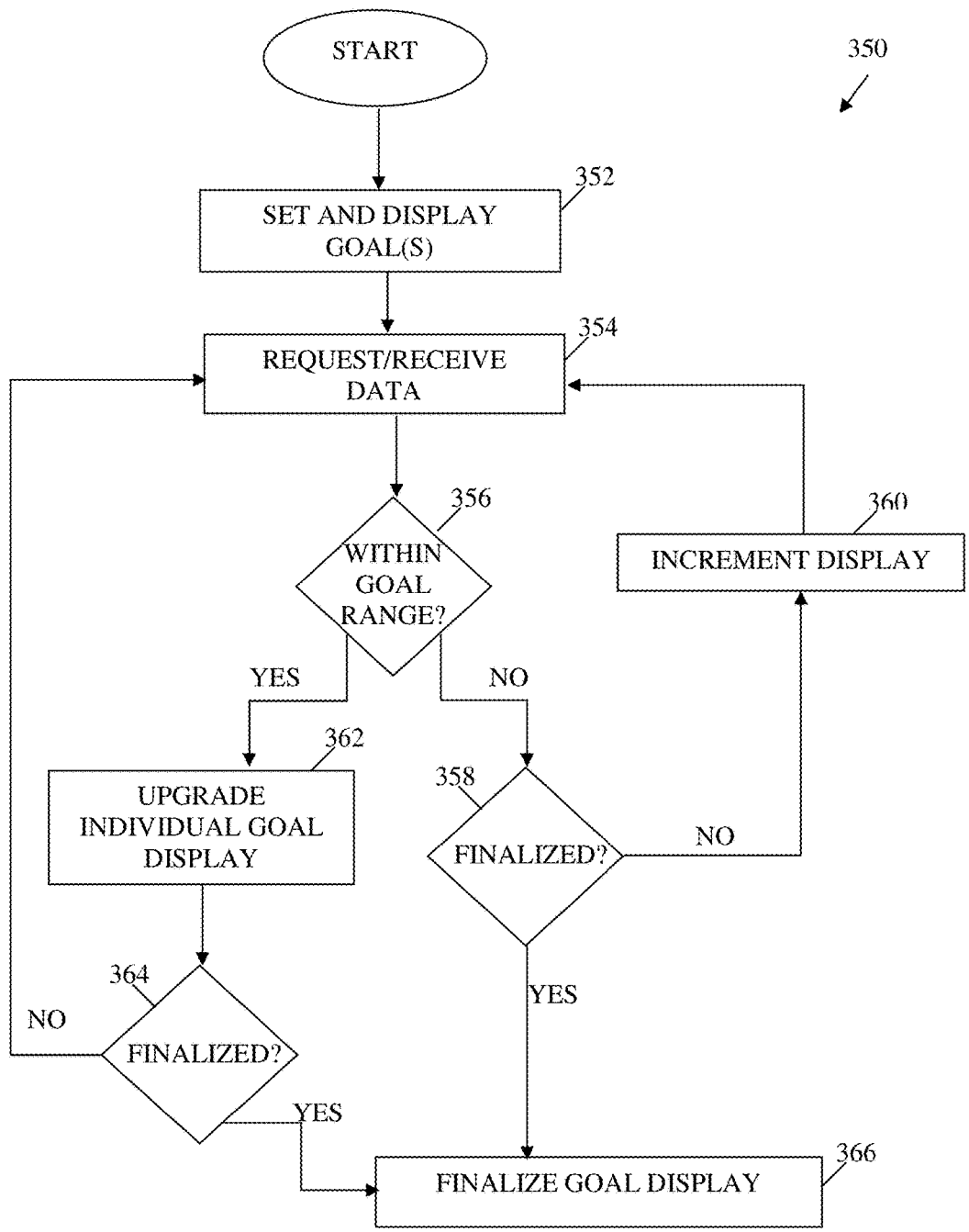
FIG. 3B is a logical flow diagram illustrating one exemplary method for managing one or more compliance range goals in accordance with the present disclosure.

Referring now to FIG. 3B, an exemplary method 350 for managing one or more compliance range goals is illustrated. As shown, per step 352, the goals are set and displayed. In one embodiment, the user may enter these goals, or they may be derived or recommended based on e.g., the type of device and/or what is known about the user (e.g., age, height, weight, etc.). The set goals are stored at the storage entity 106 and displayed at a home or start screen (prior to the user beginning progress toward meeting the goal).

Next, at step 354, measured health parameter data is requested and/or received. As noted elsewhere herein, in certain variants, the management entity 102 requests the data; alternatively, it may be provided thereto without an affirmative request. Data may be provided in real time, and/or periodically based on the type of device and/or data.

For example, the sensed data may be provided to the management entity 102 as it is collected, i.e., in real time. Alternatively, sensed data may be provided as a single so-called "data dump" at a predetermined time for each monitoring device 104. In another example, the management entity 102 may periodically request data from the monitoring devices 104 at different periods or intervals based on the type of device.

Once data has been collected, at step 356, it is determined whether the goal for that particular health parameter is within an acceptable range. As noted elsewhere herein, the acceptable range may be entered by the user at the time he/she enters the goal; and/or may be recommended or derived based on the entered goal, what is known about the user, and/or the type of device.

When the goal range is not met, at step 358, it is determined whether more data will be collected (i.e., whether the data collection is finalized). If so, the display is finalized at step 366. Optionally, the system may provide an alert and/or recommendation message to the user which may provide assistance for meeting the goal range in the future. If the data collection is not yet finalized, per step 360, the display is incremented. As discussed elsewhere herein, incrementing the display may include e.g., adjusting an amount of shading or coloring to reflect a newly calculated percent completion of the set goal. Next, the method 350 returns to step 354 where additional health parameter data is received/requested.

In the event that the goal for the particular health parameter is within the acceptable range, per step 362, the display for that health parameter is upgraded to indicate the achievement. For example, the display upgrade may include animation, change in color, highlighting, enlarging the shape, etc. Next, it is determined whether the data collection is finalized (step 364). If so, the display is finalized at step 366. If the data collection is not yet finalized, the method 350 returns to step 354 where health parameter additional data is received/requested. It is further appreciated that when all goals on a display are within the given range, the entire display may be upgraded, such as by animation, color, highlighting, etc. as noted elsewhere herein.

Although discussed herein with respect to quantifiable goals, it is appreciated that subjective goals may also be utilized consistent with the present invention. Specifically, one or more of the monitoring devices 104 may comprise devices for which values may be difficult and/or inconvenient to obtain. In this instance, the user may instead be asked to enter a subjective self-reported progress value toward the goal. For example, the user may be asked whether he/she has been active, moderate, or lazy today; whether he/she has eaten well, moderate, or poorly (such as in a first meal, second meal, snack, and/or third meal) today; and so forth for additional ones of the health parameters discussed herein. The goal which should be met would therefore be "active" or "eaten well", etc. A person of ordinary skill will understand that the discussion above regarding determining whether the goals are met and dynamically adjusting the display based on whether goals are met, incremented toward the goal, or exceeded continues to apply to these types of goals as well.

Figure 4:
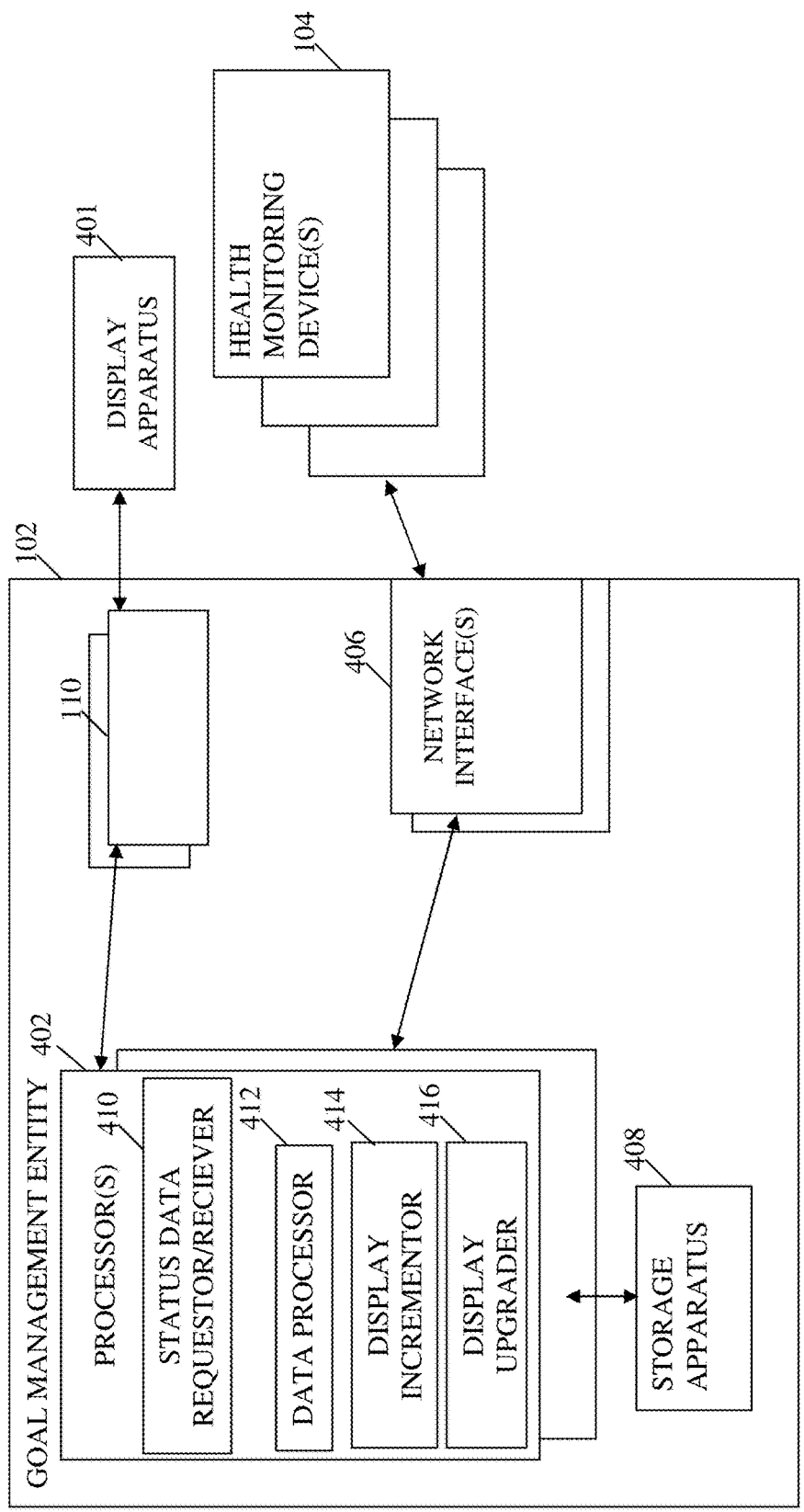
FIG. 4 is a block diagram illustrating an exemplary goal management entity in accordance with one embodiment of the present disclosure.

Referring now to FIG. 4, an exemplary goal management entity 102 is given. As discussed elsewhere herein, the goal management entity 102 in one embodiment comprises a user or client device which is configured to run one or more applications that provide the herein referenced functionality. The client or user device may comprise e.g., a smart phone, tablet, smart watch, personal computer, laptop computer or other computerized device capable of storing and/or accessing one or more software applications for providing dynamic displays. As shown, the goal management entity 102 generally includes a storage apparatus 408 and one or more processors 402, user interfaces 110, and network interfaces 406. Other components of the management entity 102 may additionally be provided to ensure functioning of the management entity 102 (not shown). In one embodiment the storage apparatus 408 corresponds to the storage entity 106 of FIG. 1. Alternatively, the storage entity 106 may comprise a separate entity than the management entity 102 (yet may be in communication therewith), and the storage apparatus 408 comprises a temporary storage facility for quick access by the management entity 102.

The user interfaces 110 comprise means by which a user can interact with various ones of the applications or programs on the management entity 102. In one embodiment, a graphic user interface (GUI) is displayed to the user via a display apparatus 401, which may be located within the goal management entity 102 or separate therefrom. For example, the GUI may be displayed on a display screen of a smart phone (in this example, the smart phone comprises the goal management entity 102). Exemplary GUI and will be provided and discussed in further detail below.

The network interfaces 406 enable communication between the health monitoring devices 104 and the goal management entity 102. Additionally, the network interfaces 406 enable communication between the goal management entity 102 and other network devices via the network 108 such as e.g., a device data warehouse, device manufacturers, etc. In one embodiment, the network interfaces 406 comprise a dedicated communication line between each health monitoring device 104 and the management entity 102 (such as via dedicated frequency bands, etc.); alternatively other well-known mechanisms may be utilized to enable communication over a shared connection.

The management entity 102 further includes one or more processors or processor cores 402 configured to run various computer applications thereon, which may be stored at e.g., the storage apparatus 408. For the purpose of this application, including the claims, the terms "processor" and "processor cores" may be considered synonymous, unless the context clearly requires otherwise. Additionally, the storage apparatus 408 may include mass storage devices such as diskette, hard drive, compact disc read only memory (CD-ROM) and so forth. Additional features of the management apparatus 102 may include e.g., input/output devices (such as display, keyboard, cursor control and so forth) and additional communication interfaces (such as network interface cards, modems and so forth), not shown. Moreover, the elements may be coupled to each other via system bus including one or more bridged busses (not shown).

The computer applications run by the processor 402 include one or more of: a data request/receive application 410, a data processing application 412, a display generation application 414, and a display upgrade application 416. Additional software applications and processes may be run at the processors 402 as well; the foregoing are merely exemplary. Moreover, the functionality described as attributable to one or more of the foregoing applications may be combined into fewer applications and/or a single application.

In one exemplary embodiment, the data request/receive application 410, the data processing application 412, the display generation application 414, and the display upgrade application 416 are run as a management application suite on a computerized device (such as a smartphone) and cooperate to provide the functionality described throughout the disclosure.

The data request/receive application 410 comprises a software process which enables the goal management entity 102 to request and receive data from the health parameter monitoring devices 104. The request/receive application 410, for example, may cause periodic requests for data to be sent to the devices 104 for sensed, obtained, or monitored information. Alternatively, the devices 104 may provide health parameter information in real-time and/or without an affirmative request from the management entity 102; the request/receive application 410 would in this embodiment additionally cause a request for information to be sent in cases where a particular device 104 has not provided data in a reasonable or preset amount of time, and/or has provided data which contains errors.

The data processing application 412 comprises a software process which enables the management entity 102 to process data. For example, the processing application 412 may enable processing of health parameter data to determine whether a goal is met and/or exceeded, whether a goal range is met, whether any additional unmet goals exist, and/or whether data collection is finalized. In addition, the processing application 412 may process requested/received data to determine whether notifications, recommendations and/or reminders should be provided to a user. It is further noted that the processing application 412 is configured to take into account user-entered preferences regarding notifications including e.g., frequency of delivery, and events which would trigger the sending of notifications.

The display generation application 414 and the display upgrade application 416 comprise software processes which cause generation of the GUI which are displayed to a user of the management entity 102. As noted elsewhere herein, changes to the GUI may be based on decisions made by the processing application 412. For example, the processing application 412 may determine that a particular notification should be displayed, this determination is sent to the display generation application 414 which then causes the display to be changed to display the particular notification. In addition, the display upgrade application 416 may be utilized to cause changes to the GUI when goals are met and/or exceeded which are referred to herein as upgrades. Selection of an appropriate upgrade may be performed by the display upgrade application 416 based on a determination at the processing application 412.

In another embodiment, a device registration application (not shown) is provided which enables the plurality of health monitoring devices 104 to register with the monitoring entity 102 and to be assigned a unique identifier for communications therewith.

In other embodiments, the foregoing applications (410, 412, 414, and 416) may be a launched via a generic browser, such as Internet Explorer, available from Microsoft Corp., of Redmond, Wash., or Safari from Apple Computer of Cupertino, Calif., e.g., such as in cases where management device 102 comprises a desktop or tablet computer. In other embodiments, the applications (410, 412, 414, and 416) may comprise client side applications, e.g., in cases where management device 102 comprises a personal digital assistant or smartphone. In such cases, the applications are stored at a storage apparatus 106 independent or separate from the management device 102 itself.

A permanent copy of the programming instructions for the aforementioned applications (410, 412, 414, and 416) may be placed into permanent storage devices (such as e.g., the storage apparatus 408 and/or storage entity 106) during manufacture of the management device 102, or in the field, through e.g., a distribution medium (not shown), such as a compact disc (CD), or through communication interface 406 (from a distribution server (not shown)). That is, one or more distribution media having an implementation of the agent program may be employed to distribute the agent and program to various computing devices.

The herein described application suite (i.e., applications 410, 412, 414, and 416) improves the functioning of the management device 102 by enabling it to provide a unified user interface which enables a user/operator to monitor his/her progress toward a number of goals related to measured health parameters which are sensed at a plurality of health monitoring devices 104. Furthermore, devices that are able to provide a dynamic display of a user's progress toward a plurality of health parameter goals can operate more efficiently to assist a user in establishing healthy lifestyle patterns.

Figure 5B:
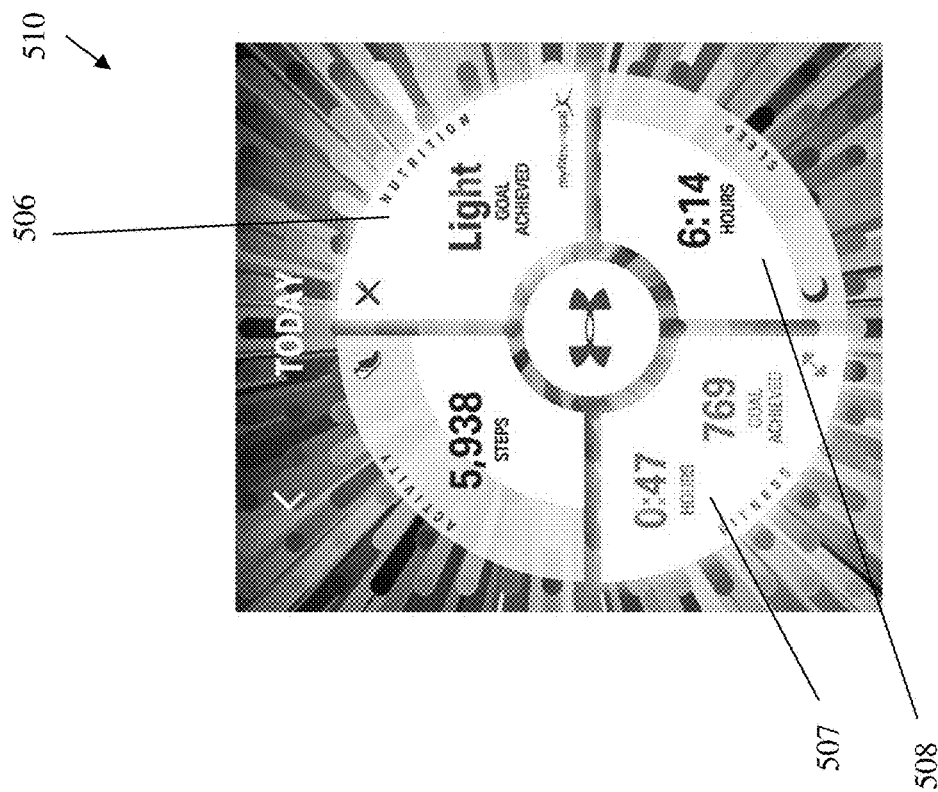
FIG. 5B is a graphical representation of an exemplary user interface showing another embodiment of the exemplary home screen which depicts completion of various ones of the displayed goals in accordance with the present disclosure.
Figure 5A:
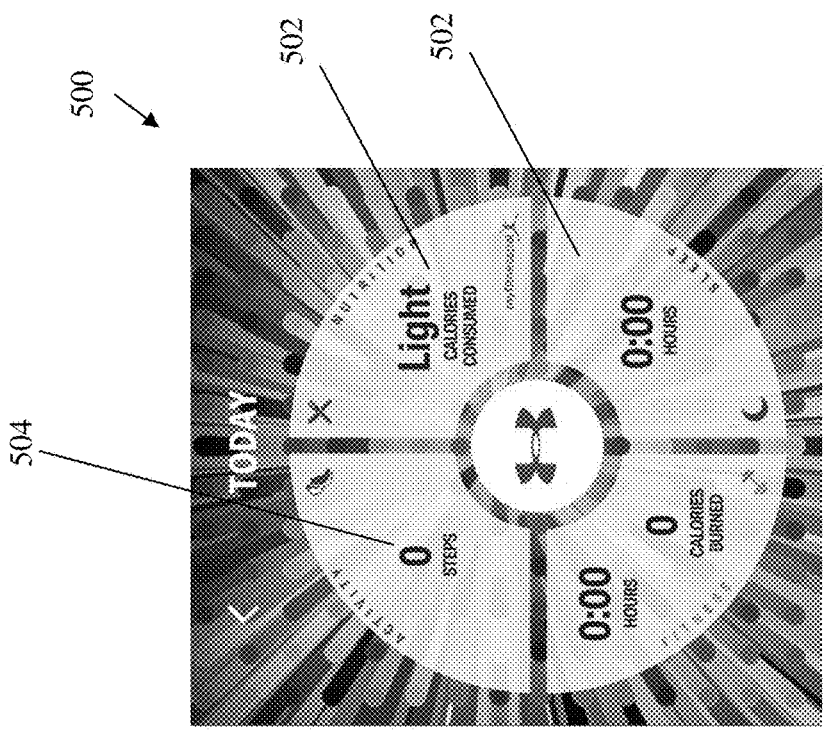
FIG. 5A is a graphical representation of an exemplary user interface showing an exemplary home screen according to one embodiment of the present disclosure.

Referring now to FIG. 5A an exemplary user interface 500 to be displayed by the management entity 102 is illustrated. Specifically, FIG. 5A illustrates an exemplary so-called "home screen" to which a user is brought when the management application suite (i.e., an application which utilizes the component applications 410, 412, 414, and 416 discussed above) is loaded or launched. As shown, the home screen 500 includes one or more indicator panels 502 which each relate to sensed, monitored, or obtained health parameter data. In one embodiment, the panels 502 are of the type illustrated in U.S. Design application Ser. No. 29/539,267, filed on Sep. 11, 2015, and incorporated herein by reference in its entirety. Each panel 502 represents a category or type of health parameter data. The panels 502 each comprise one or more text and/or numerical values 504 that describe the panel and provide information relating to the user's progress (e.g., nutrition, 0 steps, etc.). The panels 502 are further configured to change dynamically as the user works toward a goal in each category. Suppose for example that the user has taken 804 steps when he/she opens the application, in such instance, the display will indicate a portion of the panel being shaded or filled in. In one variant, the amount of shading or filling in of the portion of the annulus representative of the number of steps is proportional to the total area of the portion. In other words, when the user's goal is 10,000 steps, then 804 steps is roughly 8% accomplishment of the goal, therefore the panel is shaded or filled in by 8% of the total area. As the user continues to progress toward his/her goals, the shading or filling is adjusted dynamically.

When a goal is met, further indicators or upgrades are provided to the display. One exemplary upgraded display 510 when a user has met various ones of his/her goals is demonstrated in FIG. 5B. As shown, the user in this embodiment has met his goal for nutrition and for fitness.

In the illustrated embodiment, the panel relating to nutrition 506 is highlighted and text therein is updated to state "Goal Achieved". That is, when the goal is met, rather than a simple shading of the panel 506, the panel 506 is illuminated. In another embodiment, a color may be designated for each of the panels, such that when the goal is met, the panel (such as panel 506) is highlighted or illuminated in that color. Other options for upgraded displays include using animations, foiling, flashing, etc. may be used.

Similarly, the panel relating to fitness 507 is illustrated as having the goal relating thereto being met. As shown, the panel 507 is illustrated as being completely filled; in addition the entire panel 507 is highlighted. In one variant, the highlighting resembles illumination of the panel 507 in a particular color. Similarly, other options for upgraded displays include using animations, foiling, flashing, etc. may be used.

It is further appreciated that the herein discussed display upgrades may be performed as an animation or series of display changes that culminate in the highlighting discussed herein. For example, when the user opens home screen 500, an animation may be used to demonstrate that progress has been made in e.g., panel 506 and 507 via animated shading of these panels. As the shading reaches completion or "full", the entire panels 506 and 507 are illuminated or highlighted. In another variant, the animation may comprise a shimmer or shine which appears on the panel (e.g., 506 and/or 507). In one further variant, the shine or shimmer is constantly moving or animated.

In addition, further text, graphics, audio/video content, and flashing screens may be utilized to animate the completion of a goal.

Also demonstrated in FIG. 5B at the panel relating to sleep 508 is a further illustration of progress toward a goal. As explained above with reference to FIG. 5A, the amount of shading of the panel 508 is directly correlated to the user's progress toward the goal.

Figure 5C:
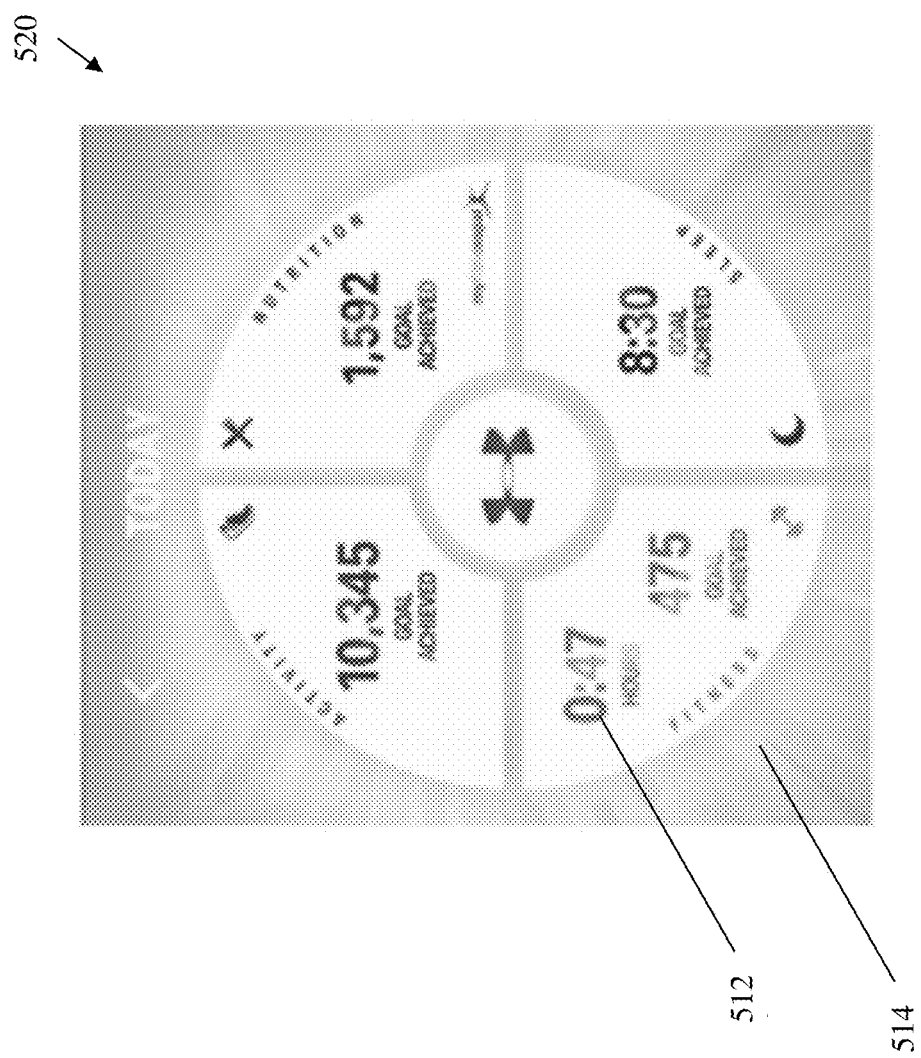
FIG. 5C is a graphical representation of an exemplary user interface showing another embodiment of the exemplary home screen which depicts completion of all of the displayed goals in accordance with the present disclosure.

FIG. 5C demonstrates an exemplary display screen 520 when the user has met the goal for all of the displayed panels. Specifically, in this embodiment, the background 514 is changed in color and pattern. In one particular example, the background 514 may be colored gold. In another particular example, the underlying pattern is replaced with a starburst or sunshine pattern (i.e., various shades of yellow or gold to create a shining effect). In another particular example, an animation may be added to the display 520 wherein all goals are met. The animation may include text, audio/video, images, flashing, shimmering or shining (as discussed above), etc. It is appreciated that the foregoing background changes in color and/or pattern may be implemented at the user meeting fewer than all of the goal panels 502, the foregoing being merely exemplary.

Referring back again to the embodiment of FIG. 5C, the measured accomplishment 512 (e.g., 8:30 of sleep, 10,345 steps taken, etc.) may be changed to a color representative of the health goal for that panel. For example, the color red may be used to signify the "activity" panel, hence the number of steps (e.g., 10,345 may be provided in red when the goal is met or exceeded).

It is appreciated that the term "met" as it is used to relate to the completion of a goal in FIGS. 5A-5C above, is intended to refer to the user's activity meeting a given threshold value, exceeding a threshold value, being within a given range of the threshold value, and/or less than the predetermined threshold value as appropriate for the particular activity and/or goal (as discussed elsewhere herein). The term "met" is therefore used merely to refer to a positive accomplishment of the user with respect to that activity.

In summary, a method of providing a dynamic display to a user at a health device is disclosed. In one embodiment, the method comprises: (i) displaying a plurality health parameters to the user each of the plurality of health parameters having a goal associated therewith; (ii) receiving a plurality of data relating to one or more of the health parameters; (iii) incrementing the display according to a progress of the user toward the goal associated to the one or more of the health parameters based on the received plurality of data; and (iv) when it is determined that collection of the plurality of data is completed, determining whether the plurality of data places a current value of a first one of the plurality of heath parameters within a predetermined range of the goal associated therewith.

Furthermore, a non-transitory, computer readable medium is disclosed. In one embodiment, the non-transitory, computer readable medium comprises a plurality of instructions which are configured to, when executed: (i) display to a user an interface comprising a plurality of portions, each of the plurality of portions of the display relating to a respective one of a plurality health parameters, having goal associated therewith, and comprising at least shading representative of a progress of the user toward the goal; (ii) receive health parameter data relating to one or more of the plurality of health parameters; (iii) update the shading representative of the progress of the user toward the goal associated to the one or more of the plurality of health parameters based on the received plurality health parameter data; and (iv) when the update to the shading representative of the progress of the user toward the goal associated to the one or more of the plurality of health parameters comprises an update to complete the shading of the portion of the display relating to at least one of the one or more of the plurality of health parameters, upgrade the display of the portion.

In addition, an apparatus for management of progress with regard to a plurality of health parameters is disclosed. In one embodiment, the apparatus comprises: at least one first interface configured to enable communication with the plurality of health devices; at least one second interface configured to provide a display to a user; a storage entity; and a processor configured to communicate with the storage entity, the at least one first interface, and the at least one second interface. In one embodiment, the processor is configured to execute at least one computer program thereon, the computer program comprising a plurality of instructions which are configured to, when executed by the processor, cause the apparatus to: (i) establish a target value for each of the plurality of health parameters; (ii) cause the at least one second interface to display a plurality of shapes, each one of the plurality of shapes being representative of an individual one of the plurality of health parameters; (iii) receive data relating a progress of the user with regard to one or more of the plurality of health parameters from the plurality of health devices; (iv) cause the individual ones of the plurality of shapes associated to the one or more of the plurality of health parameters to be filled in by an amount representative of the progress of the user toward the target value; and (v) display an animation when an individual one of the plurality of shapes is filled in completely and the target value for the health parameter associated therewith is met.

It will be appreciated that the various ones of the foregoing aspects of the present disclosure, or any parts or functions thereof, may be implemented using hardware, software, firmware, tangible, and non-transitory computer readable or computer usable storage media having instructions stored thereon, or a combination thereof, and may be implemented in one or more computer systems.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A method of providing a dynamic display to a user at a health device, said method comprising:
   displaying a plurality health parameters to said user each of said plurality of health parameters having a goal associated therewith, said goal represented by a shape with a fill amount within said shape representative of said user's progress toward said goal;
   receiving a plurality of data relating to one or more of said health parameters;
   incrementally increasing said fill amount within said shape according to a progress of said user toward said goal associated to said one or more of said health parameters based on said received plurality of data;
   when it is determined that collection of said plurality of data is completed, determining whether said plurality of data places a current value of a first one of said plurality of heath parameters within a predetermined range of said goal associated therewith;
   when it is determined that said current value of said first one of said plurality of health parameters is within said predetermined range, upgrading a portion of said display associated with said shape, wherein said act of upgrading said portion of said display associated with said shape comprises causing an animation to be displayed;
   when it is determined that collection of said plurality of data is completed, determining whether said plurality of data places a current value for each of said plurality of heath parameters within a predetermined range of said goal associated therewith; and
   when it is determined that said current value for each of said plurality of health parameters is within said predetermined range, upgrading an entirety of said display.

2. The method of claim 1, further comprising when it is determined that said collection of said plurality of data is not completed, receiving a subsequent plurality of data relating to one or more of said health parameters.

3. The method of claim 1, said animation comprising at least using color, light, or flashing to simulate a shining or shimmering of said portion of said display of said first one of said plurality of health parameters.

4. The method of claim 1, further comprising when it is determined that said current value of said first one of said plurality of health parameters is outside of said predetermined range, providing recommendations or information to said user of how to maintain said first one of said plurality of health parameters within said predetermined range.

5. The method of claim 1, wherein said act of upgrading said entirety of said display comprises causing an animation to be displayed, said animation comprising using color, light or flashing to simulate a shining or shimmering of said display.

6. The method of claim 1, wherein said act of incrementally increasing said fill amount within said shape according to said progress of said user toward said goal comprises adjusting said display using shading to indicate said progress.

7. The method of claim 1, wherein said plurality health parameters comprise at least one of: steps, nutrition, weight, fitness, and sleep.

8. The method of claim 1, wherein said plurality of data is received from at least one of: a heart rate monitor; an activity tracking device; a smart scale; a sleep tracking device; and a nutrition tracking apparatus.

9. A non-transitory, computer readable medium comprising a plurality of instructions which when executed by a computer causes said computer to:
   display to a user an interface comprising a plurality of portions, each of said plurality of portions of said display relating to a respective one of a plurality health parameters, having goal associated therewith, and comprising at least shading representative of a progress of said user toward said goal;
   receive health parameter data relating to one or more of said plurality of health parameters;
   update said shading representative of said progress of said user toward said goal associated to said one or more of said plurality of health parameters based on said received plurality health parameter data;
   when said update to said shading representative of said progress of said user toward said goal associated to said one or more of said plurality of health parameters comprises an update to complete said shading of said portion of said display relating to at least one of said one or more of said plurality of health parameters, upgrade said display of said portion; and
   when said update to said shading representative of said user's progress toward said goal associated to said one or more of said plurality of health parameters comprises an update to complete said shading of all of said portions of said display, upgrade an entirety of said display.

10. The non-transitory, computer readable medium of claim 9, wherein said upgrade comprises a change to a color used to depict at least one of said shading and said portion of said at least one of said one or more of said plurality of health parameters.

11. The non-transitory, computer readable medium of claim 9, wherein said upgrade comprises using color, light, or flashing to simulate a shining or shimmering of said display.

12. The non-transitory, computer readable medium of claim 9, wherein said upgrade to said entirety of said display comprises a change to all colors used to depict at least one of said shading and said portions of said display.

13. The non-transitory, computer readable medium of claim 9, wherein said upgrade to said entirety of said display comprises causing an animation to be displayed, said animation comprising using color, lights, or flashing to simulate a shining or shimmering of said display.

14. An apparatus for management of progress with regard to a plurality of health parameters, said apparatus comprising:
   at least one first interface configured to enable communication with a plurality of health devices;
   at least one second interface configured to provide a display to a user;
   a storage entity; and
   a processor configured to communicate with said storage entity, said at least one first interface, and said at least one second interface, said processor configured to execute at least one computer program thereon, said computer program comprising a plurality of instructions which are configured to, when executed by said processor, cause said apparatus to:
      establish a target value for each of said plurality of health parameters;
      cause said at least one second interface to display a plurality of shapes, each one of said plurality of shapes being representative of an individual one of said plurality of health parameters;

receive data relating a progress of said user with regard to one or more of said plurality of health parameters from said plurality of health devices;

cause said individual ones of said plurality of shapes associated to said one or more of said plurality of health parameters to be filled in by an amount representative of said progress of said user toward said target value; and display an animation when an individual one of said plurality of shapes is filled in completely and said target value for said health parameter associated therewith is met.

15. The apparatus of claim 14, wherein said plurality of instructions are further configured to, when executed by said processor, cause said apparatus to: display an upgraded animation when each of said plurality of shapes is filled in completely and said target values for said health parameter associated therewith are met.

16. The apparatus of claim 14, wherein said plurality of health parameters comprise at least one of: steps, nutrition, weight, fitness, and sleep.

17. The apparatus of claim 14, wherein the plurality of shapes are configured to comprise portions of a larger shape which is displayed to said user via said at least one second interface.

* * * * *